(12) United States Patent
Wein et al.

(10) Patent No.: US 9,135,729 B2
(45) Date of Patent: Sep. 15, 2015

(54) METHOD AND TOMOGRAPHY APPARATUS FOR RECONSTRUCTION OF A 3D VOLUME

(75) Inventors: Wolfgang Wein, Munich (DE); Alexander Ladikos, Eching (DE)

(73) Assignees: Duerr Dental AG, Bietigheim-Bissingen (DE); White Lion Technologies AG, Munich (DE)

( * ) Notice: Subject to any disclaimer, the term of this patent is extended or adjusted under 35 U.S.C. 154(b) by 386 days.

(21) Appl. No.: 13/544,449

(22) Filed: Jul. 9, 2012

(65) Prior Publication Data

US 2013/0010920 A1  Jan. 10, 2013

(30) Foreign Application Priority Data

Jul. 10, 2011  (EP) ..................................... 11005632

(51) Int. Cl.
*A61B 6/00* (2006.01)
*G06T 11/00* (2006.01)

(52) U.S. Cl.
CPC ............... *G06T 11/008* (2013.01); *A61B 6/583* (2013.01); *G06T 2211/424* (2013.01)

(58) Field of Classification Search
CPC ........... G06T 11/006; G06T 2211/424; G01N 23/046; G01N 2021/1787; G01N 2223/419; A61B 5/0073
USPC ............................................... 378/19, 21–27
See application file for complete search history.

(56) References Cited

U.S. PATENT DOCUMENTS

| | | | |
|---|---|---|---|
| 4,812,983 A * | 3/1989 | Gullberg et al. | 378/14 |
| 7,587,022 B1 | 9/2009 | Hsieh et al. | |
| 8,666,137 B2 * | 3/2014 | Nielsen et al. | 382/131 |
| 2005/0259780 A1 * | 11/2005 | Goodgame et al. | 378/4 |
| 2006/0072800 A1 * | 4/2006 | Bernard Deman et al. | 382/131 |
| 2009/0168952 A1 * | 7/2009 | Mori | 378/15 |
| 2010/0060509 A1 * | 3/2010 | Chambers et al. | 342/22 |
| 2012/0148136 A1 * | 6/2012 | Nielsen et al. | 382/131 |

(Continued)

FOREIGN PATENT DOCUMENTS

WO  97/49065 A1  12/1997
WO  2010/054350 A1  5/2010

OTHER PUBLICATIONS

Niessen, et al. "Standardized Evaluation Methodology for 2-D-3-D-Registration," IEEE Transactions on Medical Imaging, vol. 24, No. 9, Sep. 2005, pp. 1177-1189.

(Continued)

*Primary Examiner* — Michael Maskell
(74) *Attorney, Agent, or Firm* — Factor Intellectual Property Law Group, Ltd.

(57) ABSTRACT

A method for reconstruction of a 3D volume from a set of projection images recorded by a tomography apparatus using penetrating radiation in the field of dental medical applications takes into account a given value of at least one parameter. Simulated projection images are generated which correspond to at least a subset of the recorded projection images by simulating a projection of the penetrating radiation through the reconstructed 3D volume taking into account said given value of the at least one parameter. A re-projection error is determined by comparing the simulated projection images with the corresponding recorded projection images. The re-projection error is then minimized by changing the value of the at least one parameter and by iterating over the above steps.

23 Claims, 6 Drawing Sheets

(56) References Cited

U.S. PATENT DOCUMENTS

2012/0177274 A1* 7/2012 Koehler et al. ............... 382/131
2014/0003692 A1* 1/2014 Yared et al. .................. 382/131

OTHER PUBLICATIONS

Kyriakou, et al. "Simultaneous misalignemnt correction for approximate circular cone-beam computer tomography," Phys. Med. Bio. 53 (2008), pp. 6267-6289, UK.

* cited by examiner

METHOD AND TOMOGRAPHY APPARATUS FOR RECONSTRUCTION OF A 3D VOLUME

CROSS-REFERENCE TO RELATED APPLICATIONS

The present application claims priority to European Patent Application No. 11005632.2 filed Jul. 10, 2011. The full disclosure of this earlier application is incorporated herein by reference.

BACKGROUND OF THE INVENTION

1. Field of the Invention

The invention relates to a method for reconstruction of a 3D volume from a set of recorded projection images in the field of dental medical applications.

2. Description of Related Art

Computed tomography (CT) is a digital 3D imaging method using penetrating radiation in particular X-ray radiation to obtain internal 3D information of an object. In a first recording step of CT a volume at least partially including the object is examined by irradiating the volume with the penetrating radiation from a number of different directions and recording corresponding projection images.

For this purpose, a tomography apparatus comprising a movable radiation source and a movable radiation detector is used. By moving the radiation source and the radiation detector along a generally circular scan trajectory around the object the tomography apparatus records a series of projection images wherein for each of the projection images the scan geometry is defined by the geometric relations between the volume including the object, the radiation source and the radiation detector.

The 3D volume, more precisely the localized radiation attenuation caused by object structures in the inspected volume, is then reconstructed with different mathematical CT reconstruction methods which generally take into account the scan geometry used for the recording of the projection images. After reconstruction the resulting 3D volume is presented to the user, e.g. as a series of 2D image slices cut from the 3D volume or by means of 3D visualization techniques, allowing insights into the inner structures of the examined object.

However, because of mechanical inaccuracies of the tomography apparatus, the assumed scan geometry used during reconstruction may deviate from the actual scan geometry resulting e.g. in a non-perfect approximately circular scan. Some of these mechanical inaccuracies can be compensated with the help of time consuming calibration procedures. Others might not be compensable. For example, the tomography apparatus may be afflicted with geometrical instabilities during the scan resulting in unpredictable variations of the scan geometry. As a result, the reconstructed 3D volume will show errors or artefacts which makes the interpretation by the user more difficult and might even lead to a wrong diagnosis.

A reconstruction method of computer tomography (CT) suggested by Kyriakou et al. in Phys. Med. Biol. 53 (2008) 6267-6289 therefore improves the reconstructed 3D volume by iteratively performing the reconstruction of the 3D volume using different values for the scan geometry parameters. According to the suggested method the quality of the reconstructed 3D volume is then improved by means of minimizing its entropy, which is a measure of the information content in an image. However, it is not generally guaranteed that lower entropy corresponds to a better reconstruction. Besides, this method only allows improvement with respect to a limited number of geometric parameters of the CT scan, whereas the degree of improvement is limited.

SUMMARY OF THE INVENTION

It is therefore an object of the present invention to provide a method for reconstruction, a tomography method and a digital volume tomography apparatus as mentioned at the beginning wherein the reconstruction of the 3D volume is further improved.

Furthermore, it is an object of the present invention to provide a method to operate such an apparatus wherein a higher efficiency is achieved.

Furthermore, it is an object of the present invention to provide a computer program, a computer program product, a data carrier and a computer implementing an improved reconstruction method.

With regard to the reconstruction method this object may be achieved by a method comprising the following further steps:

b) generation of simulated projection images corresponding to at least a subset of the recorded projection images by simulating a projection of the penetrating radiation through the reconstructed 3D volume taking into account said given value of the at least one parameter;

c) determining a re-projection error by comparing the simulated projection images with the corresponding recorded projection images;

d) minimizing the re-projection error by changing the value of the at least one parameter and by repeating the steps a) to d).

Once the 3D volume has been preliminarily reconstructed using any CT reconstruction method the improved method according to the invention mathematically simulates the projection of the penetrating radiation through the preliminarily reconstructed 3D volume (forward-projection). The resulting simulated projection images are then compared to the real recorded projection images and the difference between corresponding projection images (re-projection error) is evaluated. By iteratively reconstructing the 3D volume taking into account changing parameter values this re-projection error can be minimized. Because the influence of the changed parameter values is observed with the help of a direct comparison of the simulated projection images with the recorded ones this method allows a better optimization of the 3D volume.

Throughout this application the term parameter shall not only encompass single value parameters, but also parameters comprising two or more components. For example, a parameter defining the position of a radiation source may even have a differing number of components depending on the coordinate system used. The influence of the parameters on the projections may be quite direct as e.g. a parameter specifying the source position directly in projection coordinates. However, the influence on the projections may also be more indirectly derived from parameters, such as a variable in an equation defining a complex trajectory, which is in turn used to compute the individual projection coordinates.

Generally, the method to reconstruct the 3D volume in step a) will take into account several parameters, at least one of these parameters being used for the volume optimization. Depending on the parameter, the minimization step d) may comprise any algorithm to minimize the re-projection error, e.g. a complex multi-parameter minimization algorithm or only a simple search algorithm to find the minimum. If several parameters are taken into account, it is sometimes advantageous with regard to convergence to change only one or a few of these parameters and hold the others on a given start value. Afterwards the remaining parameters can be changed.

The re-projection error as a measure of the parameter match can be defined differently depending on the parameters taken into account. A simple definition would be the square-sum of the pixel differences of the compared projection images. Another possibility for measuring the error, e.g. in connection with parameters related to detector or object motion, would be a value representing the correlation between corresponding projection images.

Generally, it has proven to give mathematically more stable results if for the reconstruction in step a) and/or the generation of the simulated projection images in step b) only a limited number (e.g. ordered subsets) of projection images is used. In particular orthogonal ordered subsets of projection images, which change from iteration step to iteration step of the reconstruction, show a good convergence behaviour.

According to a first embodiment a method is provided wherein in step a) the 3D volume is reconstructed using an algebraic reconstruction technique.

Generally, the idea of the invention to generate simulated projection images by a forward-projection from the reconstructed 3D volume and to change the values of the parameters taken into account does not depend on the method used for the reconstruction. Therefore a Feldkamp type, a statistical or a compressed-sensing based reconstruction technique could also be used. However, it is advantageous to use an algebraic reconstruction technique, because by using such a technique the simulated projection images and the re-projection error are already known from the reconstruction of the 3D volume in step a). Therefore steps a), b) and c) can partially be combined in one step.

According to another embodiment a method is provided wherein in step a) the 3D volume is reconstructed using an iterative reconstruction technique.

An iterative reconstruction technique, e.g. the ordered subset simultaneous iterative reconstruction technique (OS-SIRT) is advantageous, because it is a reconstruction technique which may be implemented efficiently on a graphical processing unit (GPU). This allows for the use of a commonly available PC to perform the repeated reconstruction for the minimization of the re-projection error.

According to another embodiment a method is provided wherein at least one parameter is a geometric parameter of the projections, in particular one or more of the following: source position, detector position, object position, detector orientation, object orientation, angular rotation increment, detector shift, detector tilt, fan angle.

Generally, the scan geometry of a projection image is defined by the geometric relations between a radiation source and a detector with respect to the 3D volume. The at least one parameter used to optimize the 3D volume can be any parameter describing an aspect of the scan geometry wherein also beam parameters like fan angle or orientation are included. Such a parameter could be a basic parameter like a coordinate component of the detector position or the source position. However, the parameter could also be a compound parameter, which would be used as a substitute of related parameters, e.g. a source-detector distance instead of the detector and source positions.

According to another embodiment a method is provided wherein at least one parameter is a radiation related parameter of the projections, in particular one or more of the following: source intensity, source spectral properties, detector spectral sensitivity, detector non-linear sensitivity, beam-hardening correction factors, radiometric calibration parameters.

A major advantage of the inventive method is that the simulation of the projection images allows to take into account all sorts of parameters related to the penetrating radiation. In principle, the complete interaction of the radiation with the material inside the volume can be simulated. By taking into account radiation related parameters during optimization the quality can be further improved. Additionally, some radiation related parameters, which may be difficult to be measured directly, can be determined indirectly by means of the optimization.

According to another embodiment a method is provided wherein at least one parameter is a global parameter influencing all of the recorded projection images and their respective simulated projection images.

A global parameter may especially be a parameter the value of which does not change from one projection image to another, e.g. source intensity, detector sensitivity or fan angle of the beam. However, the influence of a global parameter may still translate differently into the individual projection images depending on how the projection matrix coefficients are derived from the parameter. A global parameter can be global with respect to a single complete scan or global with respect to several complete scans. For example, a parameter according to the later category is the source intensity which value will most probably be constant over several scans.

According to another embodiment a method is provided wherein at least one parameter is a local parameter influencing only a single recorded projection image or a subset of the recorded projection images and their respective simulated projection images at a time.

A local parameter may especially be a parameter the value of which changes from one projection image to another. Most geometric parameters change at least to a certain extend from image to image. By changing the local parameters on an individual basis for each projection image e.g. mechanical instabilities of the tomography apparatus can be compensated for each projection image.

According to another embodiment a method is provided wherein for a local parameter the re-projection error is minimized individually for each single projection image or each subset of projection images.

For considering local parameters in the optimization, the re-projection error of each individual projection can be optimized independently given the same estimate of the reconstructed 3D volume of step a). This can be achieved by simulating for one recorded projection image different forward projections with changing parameters and evaluating the re-projection error to find the best fitting parameters. A subsequent reconstruction is then computed using all improved local parameters. This process may then be repeated until good convergence is achieved.

According to another embodiment a method is provided wherein the at least one local parameter is changed individually for each projection to compensate for object motion or tomography apparatus motion, in particular one or more of the following: translation, rotation, scaling, shearing, motion in sections, local deformations.

During a scan, not only the tomography apparatus may show mechanical instabilities, but also the patient, i.e. the object in the volume, may move. Taking into account local parameters related to the object during optimization allows determining the type and/or amount of object motion relative to the tomography apparatus. The object motion can be determined in total, e.g. a movement of the head of a patient. However, the object motion can be limited to a smaller section of the object, e.g. an opening or closing motion of the jaws. To this purpose the object in the reconstructed 3D volume might be divided and parameterized with these parameters taken into account during the optimization.

According to another embodiment a method is provided wherein for at least one parameter a time dependent progress and/or a time dependent trend is recorded.

For later use, e.g. for use with further patient datasets, the progress or trend of a parameter can be stored. In this way, in particular global parameters like source intensity or detector sensitivity, can be better evaluated, because they are based on a greater number of datasets. Furthermore, this allows using these parameters for calibration or quality control purposes.

According to another embodiment a method is provided wherein at least two parameters are interdependent and changing of the two parameters in step d) takes into account the interdependence of the at least two parameters.

In this way, the performance of the minimization regarding interdependent parameters is improved. For example the change of parameter values might take into account the dependence between the z-coordinates of the detector and the source and a tilt of the C-arm supporting the source and the detector.

According to another embodiment a method is provided wherein after minimization of the re-projection error the value of at least one parameter is used for calibration of the tomography apparatus.

In this way, a calibration parameter, e.g. the detector shift, can be automatically adjusted, if the parameter changes in a reasonable manner. This automatic calibration greatly reduces or even completely avoids the amount of work involved with calibration of the tomography apparatus.

According to another embodiment a method is provided wherein after minimization of the re-projection error the value of at least one parameter and/or the re-projection error is used for quality control.

If the parameter values determined during the optimization of the 3D volume deviate significantly from standard or calibrated values of the tomography apparatus a re-calibration or technician visit can be scheduled. Furthermore, this allows quality control of individual patient datasets. If for example too much object motion is detected, this might be indicated to the operating staff in order to schedule another scan of the patient.

According to another embodiment a method is provided wherein a calibration phantom is used.

By examining a calibration phantom and optimizing its reconstructed 3D volume the values of calibration and/or quality control parameters can be better evaluated in a controlled environment. In particular, the evaluation of the values is independent from object uncertainties. Furthermore, the use of a calibration phantom better allows the calibration of object size related parameters because the dimensions and some or all of the further properties of the calibration phantom are known.

According to another embodiment a method is provided wherein the set of recorded projection images comprises at least two subsets of projection images associated with differing rotational centers and in that the at least one parameter is an offset parameter which represents a translational offset between the rotational centers of the at least two subsets and/or a rotational offset between the at least two subsets.

A known technique to increase the field of view (FOV) of a CT apparatus is the so called stitched reconstruction. Generally, this technique includes rotating the source and the detector at least two revolutions around the object of interest, wherein the rotational center of the rotation is moved from one revolution to the other. The offset between the different rotational centers is chosen such that a certain overlap of the inspected volumes is ensured. Taking into account the offset between the rotational centers, the resulting subsets of projection images are then used to reconstruct the combined 3D volume.

Regarding the invention, it is particularly advantageous to use the stitching technique in combination with the described methods, because for good reconstruction results the offsets between the rotations have to be known as exactly as possible. By taking into account the offsets as parameters in the optimization of the reconstructed 3D volume, better results can be achieved. The offset parameters can comprise a translational offset of the rotational centers as well as a rotational offset, which may represent an angular offset between the rotations and a tilt of the rotation axis. For the described method, the rotational centers can be defined by the approximate intersection point of all center rays from the source of the penetrating radiation to the detector, the so called iso-center. The subsets do not need to contain complete revolutions, because a reconstruction is also possible with projection images of only partial revolutions. It would even be possible to constantly move the rotational center while rotating around the object. The subsets of the projection images with differing rotational centers would then be reduced to only a single projection image each. In this case one would preferably use the movement rate of the offset as an optimization parameter instead of the offset itself.

With regard to the tomography method the object of the invention is achieved with a method comprising the following further step:

reconstruction of a 3D volume using a reconstruction method according to one of the methods described above.

Generally, the above described reconstruction methods which optimize the 3D volume can be used on a standalone basis and applied on datasets of already acquired scans. However, including these reconstruction methods into a complete tomography method is advantageous in particular with respect to an automated calibration, wherein the parameter values are used to influence a subsequent scan. For example, if a low source intensity is determined from a first dataset, a radiation source control current can be raised in a subsequent scan.

With regard to the digital volume tomography apparatus the object of the invention is achieved by a tomography apparatus which comprises a data processing unit configured to use one of the above reconstruction methods to reconstruct the 3D volume.

The data processing unit can be a standalone computer like a PC or a specialized data processing unit like a clinical server comprising a graphical processing unit. Advantageously, the clinical server would be dedicated to the special task of storing the recorded projection images and reconstructing an optimized 3D volume. The image data would then be presented to the user with one or several low cost workstations. These workstations could also be used to control the tomography apparatus.

According to another embodiment a tomography apparatus is provided wherein the radiation source is a cone-beam X-ray source and the radiation detector is a flat or curved 2D detector.

Generally, the improved reconstruction methods described above can be used for any kind of tomography apparatus, e.g. for clinical full-body CT scanners. However, the described methods are particularly well suited for digital volume tomography (DVT) apparatuses using cone-beam X-rays and a 2D detector. Such DVT apparatuses are mainly used for dental applications like the planning of dental implants and are generally less expensive than full body CT apparatuses.

The mechanics of DVT apparatuses generally have a lower accuracy resulting in a higher demand for reconstruction improvements.

With regard to the method to operate the tomography apparatus the object of the invention can be achieved by a method wherein the apparatus is running the reconstruction method in an idle time between acquisitions, in particular in determined overnight time slots.

In this way, the time consuming optimizations can take place without interference with normal operation of the tomography apparatus. If there is only a standalone PC for data processing, control of the apparatus and presentation of the results, no extra computing power is necessary, because the demanding computations are shifted to time slots without any user interaction. It is also possible to perform more complete optimizations in such overnight time slots, which take into account more parameters or more thoroughly search the parameter space for the absolute minimum of the re-projection error, e.g. for the fine tuning of calibration parameters.

With regard to the computer program, the computer program product, the data carrier and the computer, the object of the invention is achieved by a computer program which is configured, if running on a computer, to cause the computer to perform any of the described methods, by a computer program product comprising the computer program, by a data carrier on which the computer program is stored and by a computer on which the computer program is installed.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

Various features and advantages of the present invention may be more readily understood with reference to the following detailed description taken in conjunction with the accompanying drawing in which.

DETAILED DESCRIPTION OF THE PRESENT INVENTION

Figure 1:
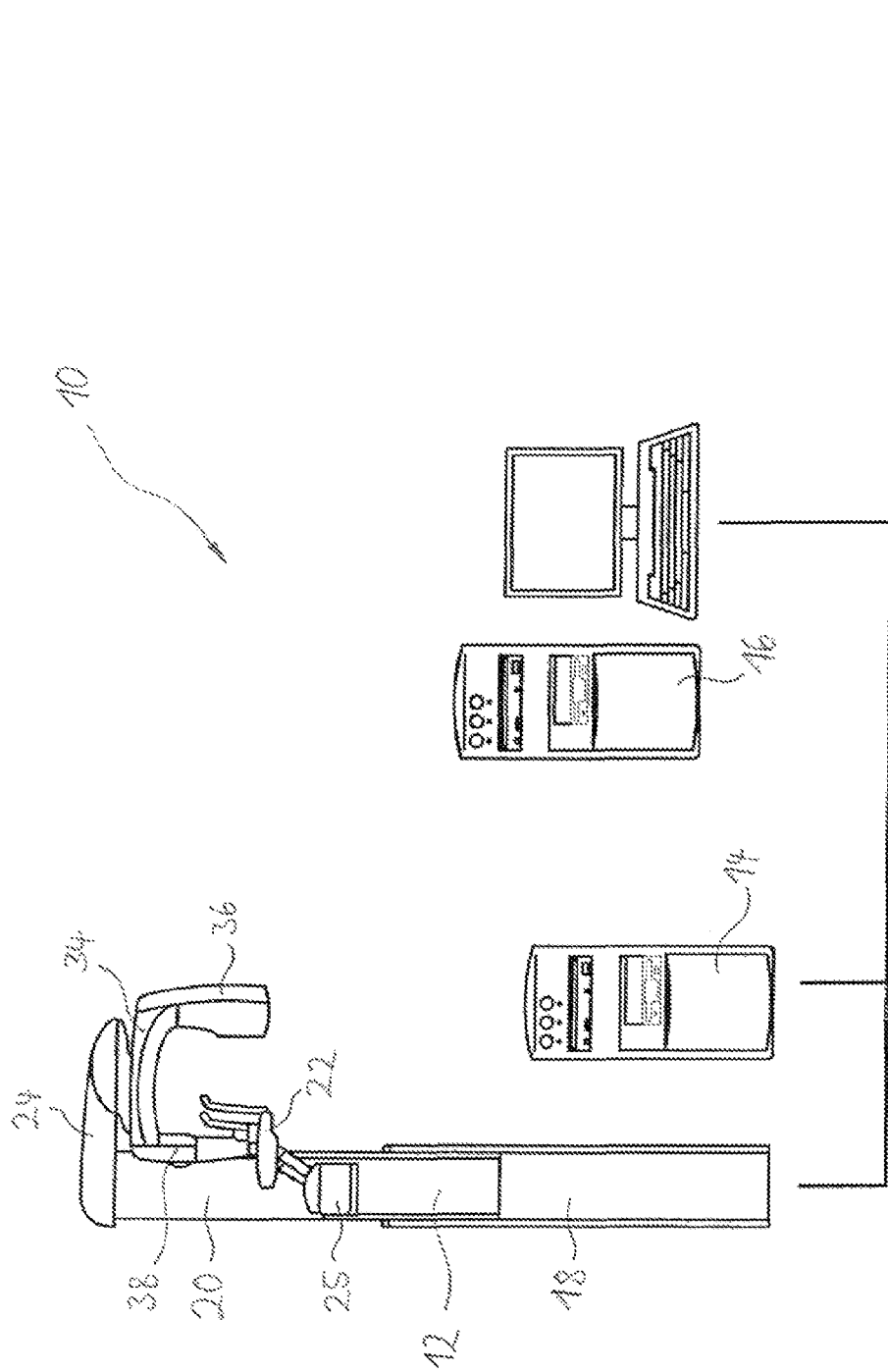
FIG. 1 shows a schematic representation of a digital volume tomography (DVT) apparatus comprising an acquisition unit, a data processing unit and a workstation for user control.

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

FIG. 1 shows a DVT apparatus 10 used for dental medical examinations of the jaw section of a patient comprising an acquisition unit 12, a data processing unit 14 and a workstation 16.

The acquisition unit 12 comprises a fixed support column 18 along which a support carrier 20 is movable in a vertical direction in order to adjust the acquisition unit 12 for different patient heights. The support carrier 20 comprises an object support beam 22 and a scanner support beam 24 which both extend horizontally from the support carrier 20. Furthermore, a control panel 25 is attached to the support carrier 20 allowing control of the acquisition unit 12, in particular for positioning the support carrier 20 along the support column 18 and for choosing different acquisition procedures.

Figure 2:
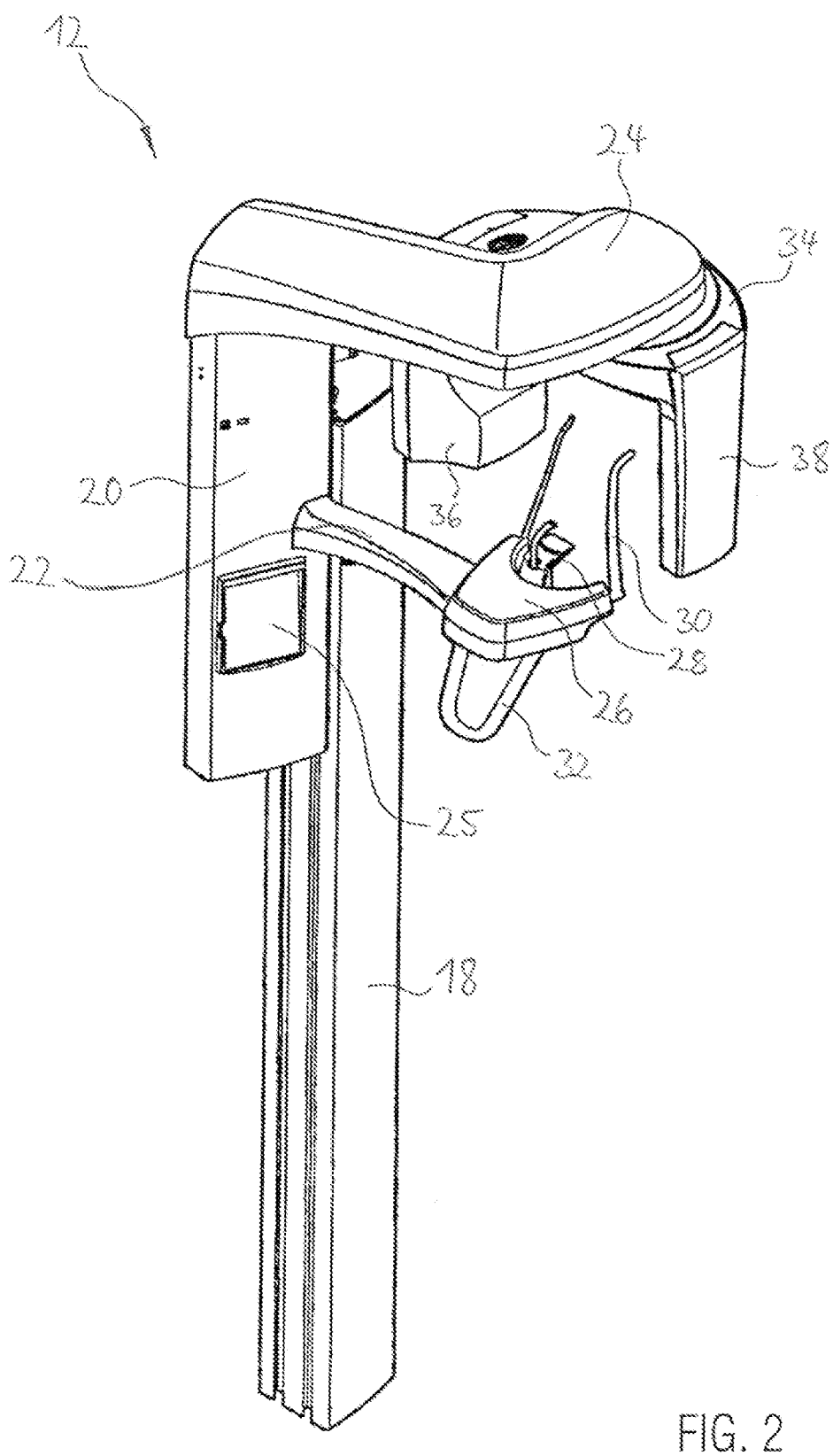
FIG. 2 shows a perspective view of the DVT apparatus.
Figure 3:
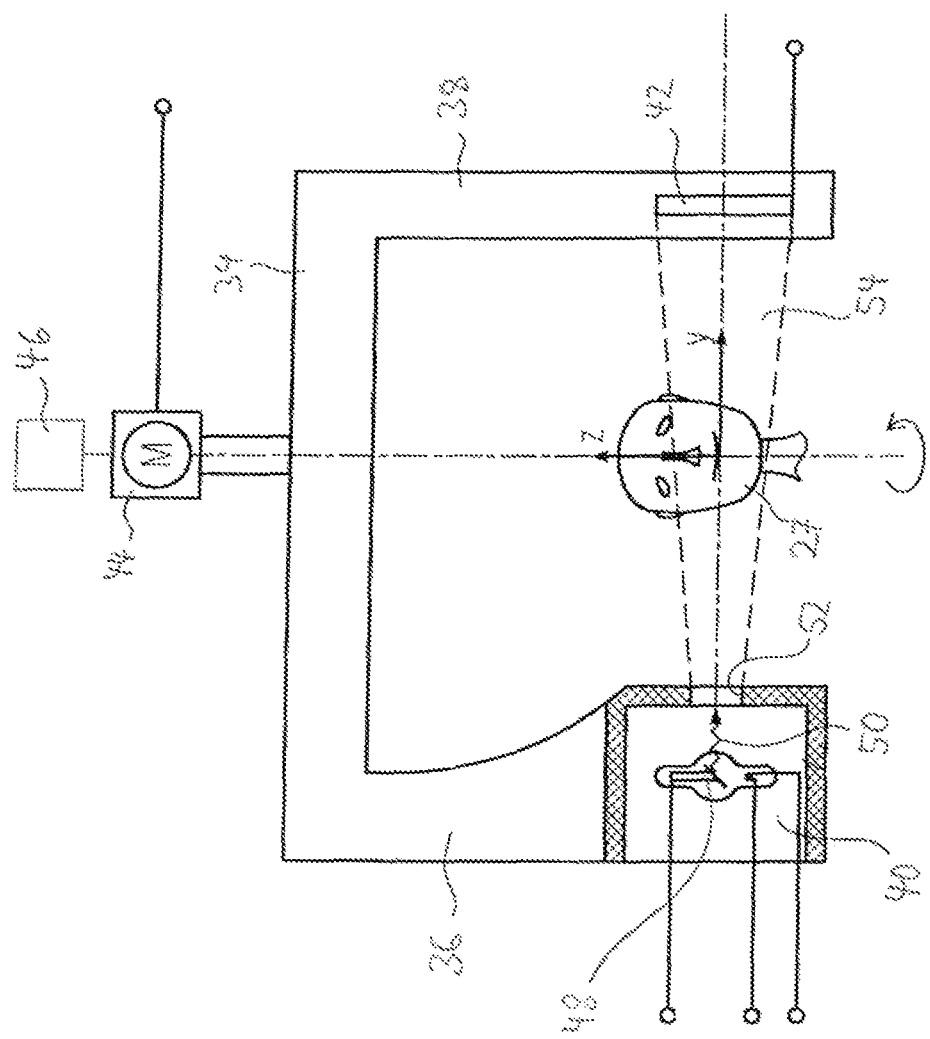
FIG. 3 shows a sectional view of the DVT apparatus.

As shown in FIG. 2, the object support beam 22 comprises a head positioning instrument 26 at its free end in order to allow an exact and comfortable positioning of a patient's head 27 (see FIG. 3). For this purpose, the head positioning instrument 26 comprises a bite plate 28 and two temple fixing braces 30. Furthermore, the head positioning instrument 26 comprises a handle 32 which allows a patient to hold tight to a certain position during the scan once the head position is fixed.

The scanner support beam 24 is arranged above the object support beam 22 and oriented such that its free end is centered approximately above the head position defined by the head positioning instrument 26. A rotary arm, the so called C-arm 34, is rotatably connected to the free end of the scanner support beam 24, the C-arm 34 being oriented such that two legs 36, 38 of the C-arm 34 point downwards.

As shown in FIG. 3, the leg 36 of the C-arm 34 supports an X-ray source 40. The other leg 38 supports a 2D pixel detector 42 which is sensitive to the radiation generated by the X-ray source 40. The rotation of the C-arm 34 is driven by a motor 44 which is arranged in the scanner support beam 22. The actual rotational position of the C-arm 34 is measured with a sensor 46. Although FIG. 3 shows a direct axial connection between the motor 44, the sensor 46 and the C-arm 34, most acquisition units 12 will comprise a rotatable connection which supports the C-arm 34 and a separate transmission gear coupling with the motor 44 for driving the C-arm 34 with high precision.

The X-ray source 40 comprises an X-ray anode 48 generating the X-ray radiation 50 and a diaphragm 52 defining the angle of an X-ray cone-beam 54 leaving the X-ray source 40 towards the detector 42 on the other leg 38 of the C-arm 34.

Figure 4:
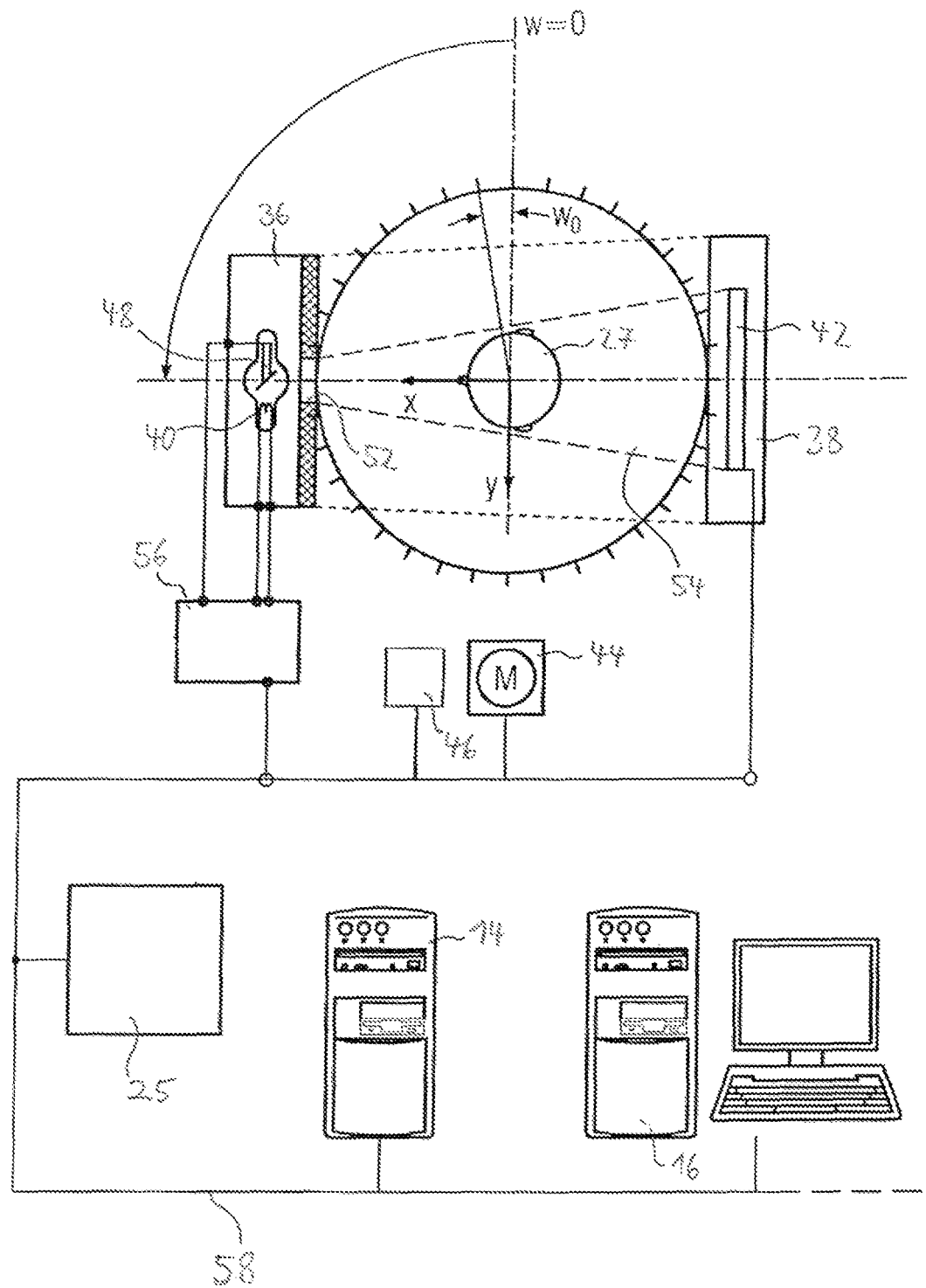
FIG. 4 shows a cross-sectional view of the DVT apparatus.

As shown in the schematic top view of FIG. 4, the X-ray source 40, the detector 42, the motor 44, the sensor 46, the control panel 25 and other electronic components like a source power supply 56 or other sensors (not shown) are connected by an electronic control bus 58 e.g. LAN, WLAN or other data transmission networks. Furthermore, the data processing unit 14 and the workstation 16 are connected to this control bus 58.

In this embodiment, the data processing unit 14 and the workstation 16 are provided as commonly available state of the art computers comprising a graphical processing unit (GPU). A GPU is a processing unit having a high computational power for problems which can be executed well in parallel. However, in particular for the data processing unit 14, special purpose electronic boards might also be used which can be included in the tomography apparatus 10.

During operation the tomography apparatus 10 works as follows:

Depending on the section to be examined the patient's head 27 is positioned and a scan program is chosen from the control panel 25. With the help of the motor 44 the C-arm 34 is then rotated stepwise in angular increments $w_0$ around the patient's head 27. Each time the C-arm 34 has reached a desired angular position the X-ray source 40 is activated and a projection image $X_i$ is acquired with the detector 42. The acquired projection image $X_i$ is then recorded in a storage of the data processing unit 14. Each recorded projection image $X_i$ has a number $N_L$ of pixels which corresponds to the number of pixels of the 2D detector 42.

Figure 5:
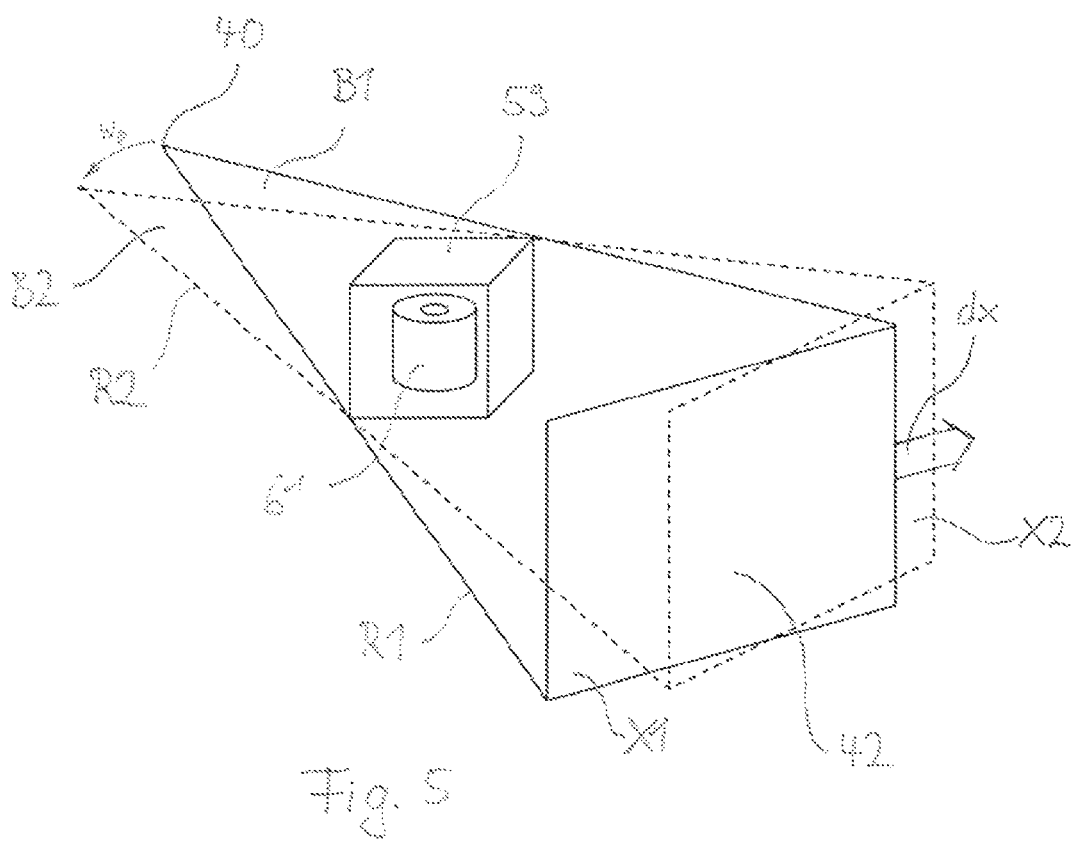
FIG. 5 shows a perspective view of the geometric relations between the 3D volume and the projection images.

FIG. 5 shows the geometric relations of the X-ray source 40, an inspected volume 59 and the detector 42 exemplarily for two subsequent projection images X1 and X2 out of the entire set of projection images $X_i$. Instead of the patient's head 27, FIG. 5 shows a calibration phantom 61 positioned in the inspected volume 59. Such a calibration phantom 61 has a precisely defined shape and known dimensions and can be used to calibrate the tomography apparatus 10 with a high precision.

A conical beam B1 of X-rays originating from the X-ray source 40 is directed through the volume 59 and is received with the detector 42. The conical beam B1 comprises a corresponding number $N_L$ of individual projected rays R1 which form the projection image X1 on the detector 42. A second conical beam B2 is directed through the volume 59 after rotation of the C-arm 34 about an angle increment $w_0$. Consequently, the conical beam B2 comprises the projected rays R2 which form the projection image B2. As becomes clear from FIG. 5, the dimensions of the detector 42 respectively the bounding projected rays therefore define the inspected volume 59 around the iso-center of the projection.

FIG. 5 also shows a small arrow representing a detector shift dx of the detector 42 with respect to the rotation center of the C-arm 34. Once the detector 42 is attached to the leg 38 of the C-arm 34 the detector shift dx is fixed and will not change from one projection image $X_i$ to another.

After all projection images $X_i$ have been recorded a set of recorded projection images $X_i$ is available to the data processing unit 14.

In the following an optimization method is described which could generally be used with global parameters like the detector shift dx or local parameters like the angular increment $w_0$. However, because the angular increment $w_0$ may differ for each projection image $X_i$ it would be computationally very expensive to optimize over all the individual parameters at once. Therefore a better optimization method for local parameters like the angular increment $w_0$ is described later.

Figure 6:
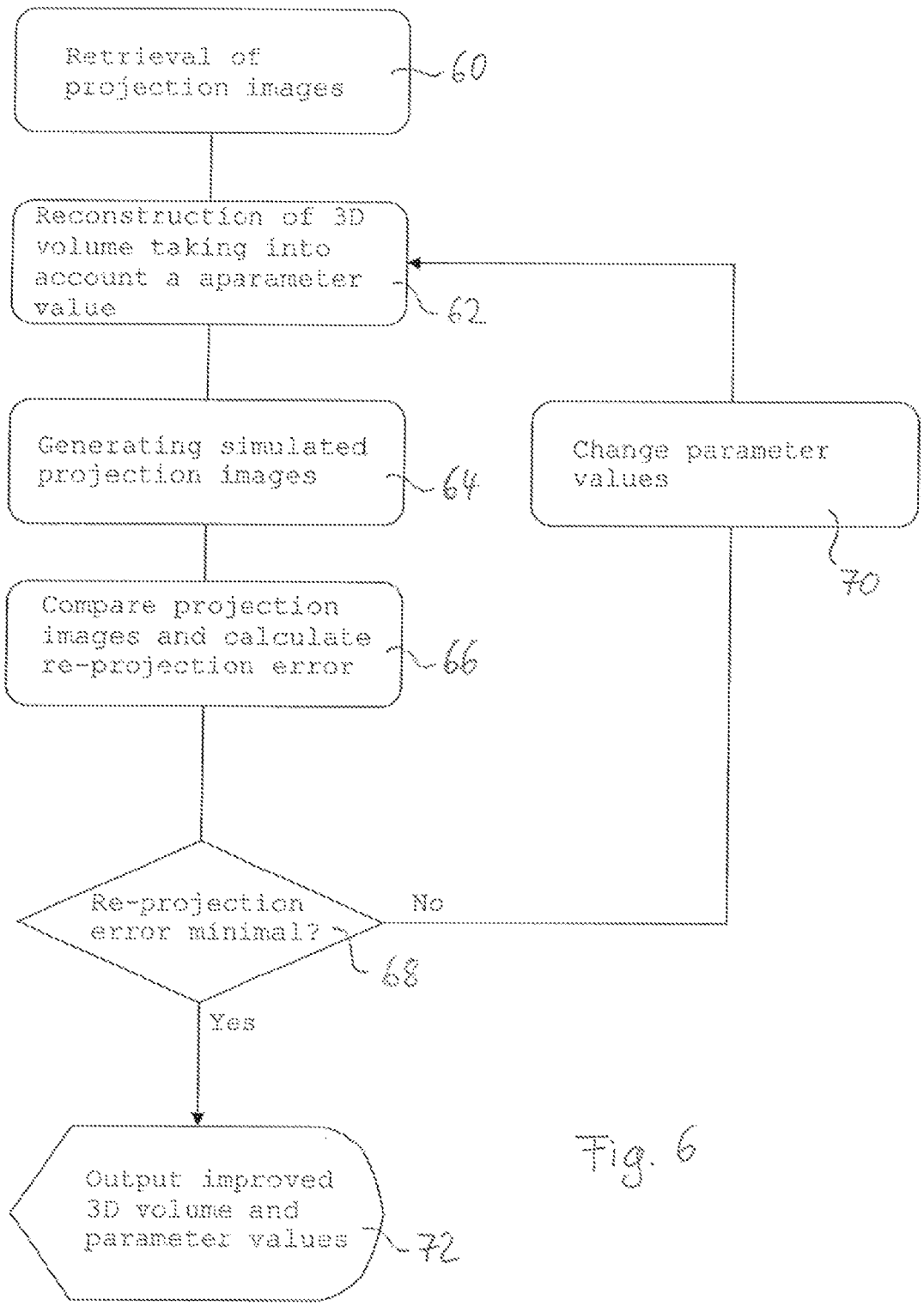
FIG. 6 shows a work flow diagram illustrating the main steps involved with the reconstruction of the 3D volume.

FIG. 6 shows a flow diagram representing the steps taken by the data processing unit 14 for obtaining an improved 3D volume reconstruction.

In a first retrieval step 60 the recorded projection images $X_i$ are retrieved from the storage, e.g. from a clinical storage server.

Following, in a reconstruction step 62 the 3D volume is reconstructed with an ordered subset simultaneous iterative reconstruction technique, wherein in the present example the angle increment $w_0$ and the detector shift dx are taken into account as projection parameters.

Afterwards, a subset of simulated projection images $X_i$ is generated in a simulation step 64. In this simulation step 64 the subset of simulated projection images $X_i$ comprises a smaller number, advantageously 8, 10 or 16, of projection images $X_i$ which are as orthogonal as possible to each other.

In a comparison step 66 the simulated projection images $X_i$ are compared with the corresponding recorded projection images $X_i$. In the present embodiment this is done with a simple subtraction of corresponding projection images $X_i$. The pixel values of the resulting difference images are squared and summed all together resulting in a re-projection error.

In a loop step 68 is evaluated if the re-projection error is smaller than a certain limit or if the re-projection error has converged. If not, the data processing unit 14 proceeds to a parameter variation step 70.

In this parameter variation step 70 the value of the parameter, in this case the detector shift dx, is changed according to a simple search algorithm.

Afterwards, the iterative loop is closed by jumping back to the reconstruction step 62. This loop is iterated as long as the conditions set for the re-projection error in comparison step 66 are not met. As soon as theses conditions are fulfilled the improved reconstruction of the 3D volume and the values of the parameters are stored and presented to the operating staff using the workstation 16.

In order to optimize the 3D volume over the angular increment $w_0$ only the simulation step 64 and the comparison step 66 would be iterated in an inner loop for each individual projection image $X_i$. By minimizing the re-projection error per projection image the best fitting angular increments $w_0$ can be found without re-running the reconstruction step 62 in this inner loop. Only after all angular increments $w_0$ of all the projection images $X_i$ have been found, another reconstruction of the volume is calculated taking into account these optimized angular increments $w_0$. This outer loop, which corresponds to the one shown in FIG. 6, can be run several times until the overall re-projection error is minimized.

In an automatic calibration mode the final values of the parameters are stored for later use in subsequent scans. In particular, when the set of recorded projection images $X_i$ are obtained from a scan of the calibration phantom 61 the values of the parameters can be determined with high precision. Furthermore, the values can be cross-checked with values expected for the calibration phantom 61.

In order to perform a stitched reconstruction the tomography apparatus 10 can have drive means to shift the rotation axis of the source 40 and the detector 42 relative to the object of interest. Here, this can be achieved by moving the head positioning instrument 26 or by moving the rotation center of the C-arm 34.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A method for reconstruction of a 3D volume from recorded projection images, wherein the method comprises the following steps:
   a) providing a set of recorded projection images that have been recorded with a tomography apparatus using penetrating radiation;
   b) providing values of at least two parameters;
   c) reconstructing the 3D volume from the set of recorded projection images, thereby using the values of the at least two parameters;
   d) generating simulated projection images, wherein each simulated projection image corresponds to one of the recorded projection images, by simulating projections of the penetrating radiation through the reconstructed 3D volume, thereby using the values of the at least two parameters;
   e) determining a re-projection error by comparing the simulated projection images with the corresponding recorded projection images;
   f) changing the values of the at least two parameters, thereby taking into account the interdependence of the at least two parameters, and repeating the steps c) to f) until the re-projection error is minimized;
wherein the method is used in the field of dental medical applications.

2. The method according to claim 1, wherein in step c) the 3D volume is reconstructed using an algebraic reconstruction technique.

3. The method according to claim 1, wherein in step c) the 3D volume is reconstructed using an iterative reconstruction technique.

4. The method according to claim 1, wherein the at least one parameter is a geometric parameter.

5. The method according to claim 4, wherein the geometric parameter is contained in the group consisting of: source position, detector position, object position, detector orientation, object orientation, angular rotation increment, detector shift, detector tilt, fan angle.

6. The method according to claim 1, wherein the at least one parameter is a radiation related parameter.

7. The method according to claim 6, wherein the radiation related parameter is contained in the group consisting of: source intensity, source spectral properties, detector spectral sensitivity, detector non-linear sensitivity, beam-hardening correction factors, radiometric calibration parameters.

8. The method according to claim 1, wherein the at least one parameter is a global parameter associated with all of the recorded projection images and the simulated projection images.

9. The method according to claim 1, wherein the at least one parameter is a local parameter that is associated with only a single recorded projection image or a subset of the recorded projection images and with the simulated projection images that correspond to the single recorded projection image or the subset of the recorded projection images.

10. The method according to claim 9, wherein for the local parameter the re-projection error is minimized individually for each single projection image or each subset of projection images.

11. The method according to claim 9, wherein the local parameter is changed individually for each projection to compensate for a motion of the tomography apparatus or for a motion of an object that has been imaged by the tomography apparatus.

12. The method according to claim 11, wherein the local parameter is changed individually for each projection to compensate at least one of the group consisting of: translation, rotation, scaling, shearing, motion in sections, local deformations.

13. The method according to claim 1, wherein, after step f), the at least one parameter is recorded, and wherein, on the basis of the at least one parameter recorded after reconstructions of different 3D volumes, a time dependent progress and/or a time dependent trend of the at least one parameter is determined.

14. The method according to claim 1, wherein after minimization of the re-projection error the value of the at least one parameter is used for calibration of the tomography apparatus.

15. The method according to claim 1, wherein, after the re-projection error has been minimized in step f), the value of the at least one parameter and/or the re-projection error is used for quality control.

16. The method according to claim 14, wherein a calibration phantom is used.

17. The method according to claim 1, wherein the recorded projection images comprise at least two subsets of projection images associated with differing rotational centers, and wherein the at least one parameter is an offset parameter which represents a translational offset between the rotational centers of the at least two subsets and/or a rotational offset between the at least two subsets.

18. The method according to claim 1, wherein in step b) the value of the at least one parameter is provided by taking a stored value of the at least one parameter which has been stored together with the recorded projection images.

19. A tomography method, comprising the following steps:
recording projection images using a tomography apparatus;
reconstructing a 3D volume using the method according to claim 1;
wherein the method is used in the field of dental medical applications.

20. An apparatus,
wherein the apparatus is a digital volume tomography apparatus that is configured to examine a 3D volume in dental medical applications and comprises a radiation source for generating penetrating radiation and a radiation detector,
wherein the apparatus further comprises a data processing unit configured to carry out the method according to claim 1 to reconstruct the 3D volume.

21. The apparatus according to claim 20, wherein the radiation source is a cone-beam X-ray source and the radiation detector is a flat or curved 2D detector.

22. A method to operate the apparatus according to claim 20, wherein the apparatus is running the reconstruction method in an idle time between recordal of images.

23. A computer on which a computer program configured to cause performance of the method of claim 1 is installed.

* * * * *